United States Patent
Mukai et al.

(10) Patent No.: US 9,271,881 B2
(45) Date of Patent: Mar. 1, 2016

(54) ABSORBENT LAYER FOR DISPOSABLE WEARING ARTICLE AND METHOD FOR MAKING THE SAME

(75) Inventors: Hirotomo Mukai, Kanonji (JP); Takaya Arayama, Kanonji (JP)

(73) Assignee: UNICHARM CORPORATION, Ehime (JP)

( * ) Notice: Subject to any disclaimer, the term of this patent is extended or adjusted under 35 U.S.C. 154(b) by 165 days.

(21) Appl. No.: 13/878,656

(22) PCT Filed: Dec. 22, 2011

(86) PCT No.: PCT/JP2011/007237
§ 371 (c)(1),
(2), (4) Date: Apr. 10, 2013

(87) PCT Pub. No.: WO2012/086210
PCT Pub. Date: Jun. 28, 2012

(65) Prior Publication Data
US 2013/0267924 A1    Oct. 10, 2013

(30) Foreign Application Priority Data

Dec. 22, 2010  (JP) ................................. 2010-286757
Nov. 28, 2011  (JP) ................................. 2011-259431

(51) Int. Cl.
*A61F 13/15*    (2006.01)
*A61F 13/534*    (2006.01)
*A61F 13/533*    (2006.01)
*A61F 13/536*    (2006.01)

(52) U.S. Cl.
CPC ......... *A61F 13/534* (2013.01); *A61F 13/15617* (2013.01); *A61F 13/533* (2013.01); *A61F 13/536* (2013.01)

(58) Field of Classification Search
CPC ................ A61F 2013/1543; A61F 2013/5355; A61F 2013/5326; A61F 2013/530934; A61F 13/535; A61F 13/536; A61F 13/532; A61F 13/53717; A61F 13/530934; A61F 13/15617; A61F 13/534
See application file for complete search history.

(56) References Cited

U.S. PATENT DOCUMENTS

| | | |
|---|---|---|
| 2001/0007936 A1 * | 7/2001 | Shimoe et al. ........... 604/385.24 |
| 2006/0069371 A1 * | 3/2006 | Ohashi et al. ........... 604/385.01 |
| 2012/0041405 A1 * | 2/2012 | Alkmin et al. ................. 604/383 |

FOREIGN PATENT DOCUMENTS

| | | |
|---|---|---|
| JP | 2003290281 A | 10/2003 |
| JP | 2004248706 A | 9/2004 |
| JP | 2009131417 A | 6/2009 |
| JP | 4439165 B2 | 3/2010 |

OTHER PUBLICATIONS www.dictionary.com/browse/reference/dimensions, May 4, 2015.*
International Search Report issued in PCT/JP2011/007237 on Feb. 21, 2012.

* cited by examiner

*Primary Examiner* — Bradley Philips
(74) *Attorney, Agent, or Firm* — Hauptman Ham, LLP

(57) ABSTRACT

An absorbent layer has a front section lying on the side of a front waist region, a rear section lying on the side of a rear waist region and an intermediate section lying between the front and rear sections. The absorbent layer is formed in the intermediate section with a central depression extending in a longitudinal direction Y and a high density zones having density higher than those of the front and rear sections are formed on both sides of the central depression.

7 Claims, 15 Drawing Sheets

ABSORBENT LAYER FOR DISPOSABLE WEARING ARTICLE AND METHOD FOR MAKING THE SAME

RELATED APPLICATIONS

The present application is a National Phase of PCT/JP2011/007237, filed Dec. 22, 2011, and is based on, and claims priority from, Japanese Application No. 2011-259431, filed Nov. 28, 2011 and Japanese Application No. 2010-286757, filed Dec. 22, 2010.

TECHNICAL FIELD

The present disclosure relates to absorbent layers for disposable wearing articles and methods for making the same and, more particularly, to absorbent layers including one or more absorbent cores and for the disposable wearing articles such as toilet-training pants, incontinent briefs or the like and methods for making the same.

BACKGROUND

Absorbent layers for disposable wearing article are known including one or more absorbent cores. For example, JP 4439165 B (PTL 1) discloses a chassis defining an outer surface of the article and an absorbent layer lying on a skin-facing side of the chassis and extending across a crotch region into front and rear waist regions. According to the disclosure of PTL 1, the absorbent layer includes an absorbent core and a pair of core supporting members adapted to support the absorbent layer from a non-skin-facing side of the absorbent layer.

CITATION LIST

Patent Literature

{PTL 1} JP 4439165 B

SUMMARY

Technical Problem

According to the absorbent layer disclosed in PTL 1, in the crotch region of the disposable wearing article, the core supporting members provided on the non-skin-facing side of the absorbent core are formed of material having absorbability and shape retention performance and therefore the article being put on the wearer's body is unlikely to be twisted or lose shape. In a clearance defined between the core supporting members, central crotch elastic elements are arranged so that the absorbent core may be kept in close contact with the wearer's body under contraction of the central crotch elastic elements. Accordingly, stiffness of the absorbent layer can be locally varied only in the crotch region by locating the core supporting means on the non-skin-facing side of the absorbent core.

However, the inventor(s) has/have noted that this wearing article of PTL 1 requires additional members for this purpose, and eventually the manufacturing cost thereof might be correspondingly increased and/or the manufacturing process might be correspondingly complicated. In addition, the stiffness value might be significantly higher in the front and rear regions in which the core supporting means are located than in the region formed only by the absorbent core. Because of such significant stiffness difference, the absorbent core might be partially folded and such folded region might come in contact with the wearer's body, creating a discomfort feeling against the wearer and causing leakage of bodily fluids.

A first aspect in accordance with embodiments of the present invention relates to an absorbent layer for a disposable wearing article having a longitudinal direction and a transverse direction orthogonal to the longitudinal direction, and comprising a front region and a rear region.

The absorbent layer includes an absorbent core formed from at least one of fluff wood pulp and superabsorbent polymer particles, and has transversely extending front and rear end sections and an intermediate section lying between the front and rear end sections; at least the intermediate section of the absorbent layer is formed with a central depression extending in the longitudinal direction; the absorbent core has a mass per unit area substantially uniform over an entire area thereof, except in a region corresponding to the central depression; and the absorbent layer has, on both sides of the central depression, high density zones each having a density higher than those in the front and rear end sections.

A second aspect in accordance with some embodiments of the present invention relates to a method for making an absorbent layer for a disposable wearing article comprising the steps of:

successively depositing absorptive materials including at least one of fluff wood pulp and superabsorbent polymer particles into recessed molds, which are formed on an outer peripheral surface of a rotary suction drum and centrally provided with protrusions, to mold absorbent cores having a substantially uniform thickness over the whole areas thereof, except in central depressions corresponding to the protrusions, and respectively having intermediate sections narrower than front and rear end sections thereof;

successively conveying the pre-formed absorbent cores in a machine direction; and at a press-working station including a press roller set arranged to exert a predetermined force to a rotary shaft of an anvil roller provided in opposition to the press roller, successively guiding the pre-formed absorbent cores into a clearance defined between the press roller and the anvil roller for press-working the respective absorbent cores and forming the intermediate sections of the respective absorbent cores with high density zones on both sides of the respective central depressions.

DESCRIPTION OF EMBODIMENTS

First Embodiment

Details of the disposable wearing articles according to a first embodiment of the present invention will be more fully understood from the following description of a disposable diaper 10, a typical example of the disposable wearing article, with reference to the accompanying drawings.

Figure 1:
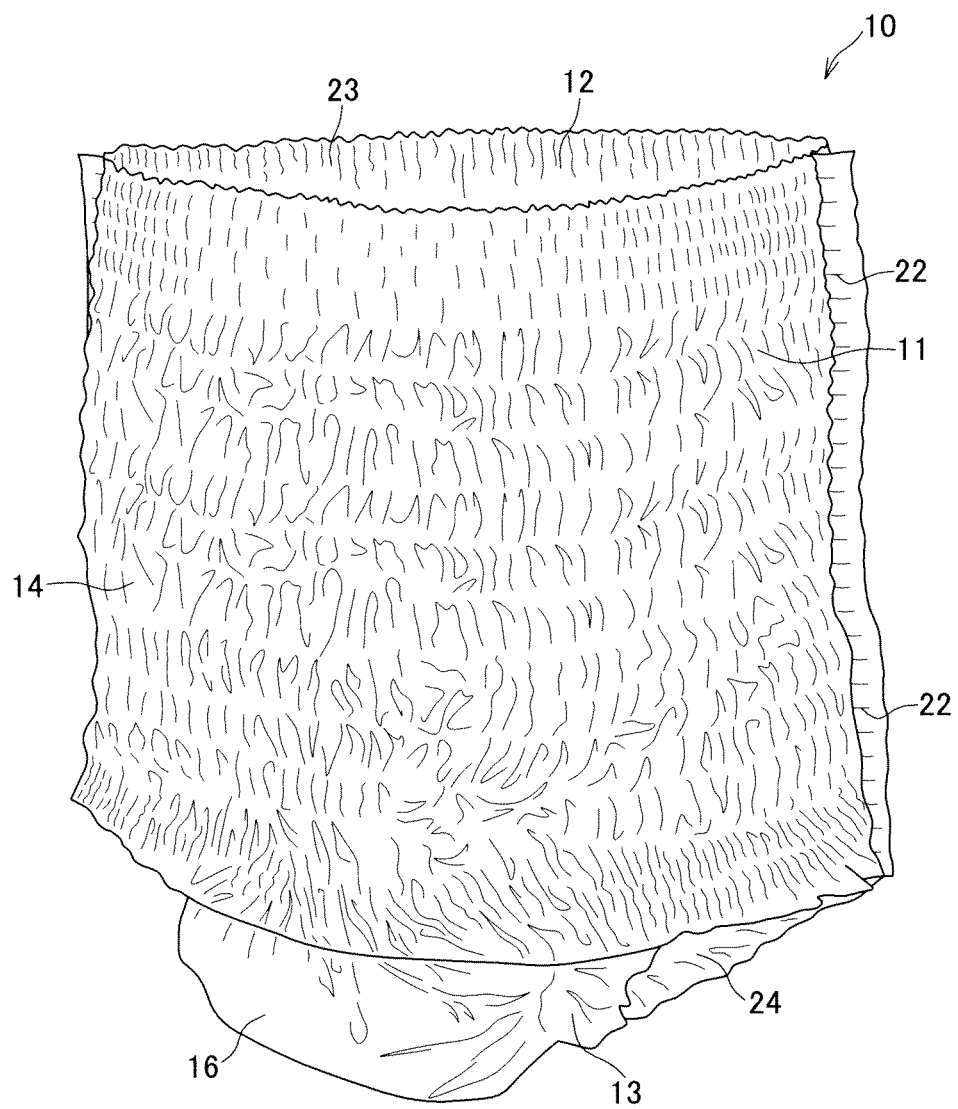
FIG. 1 is a perspective view of a disposable diaper as a typical example of a disposable wearing article according to a first embodiment of the present invention.
Figure 2:
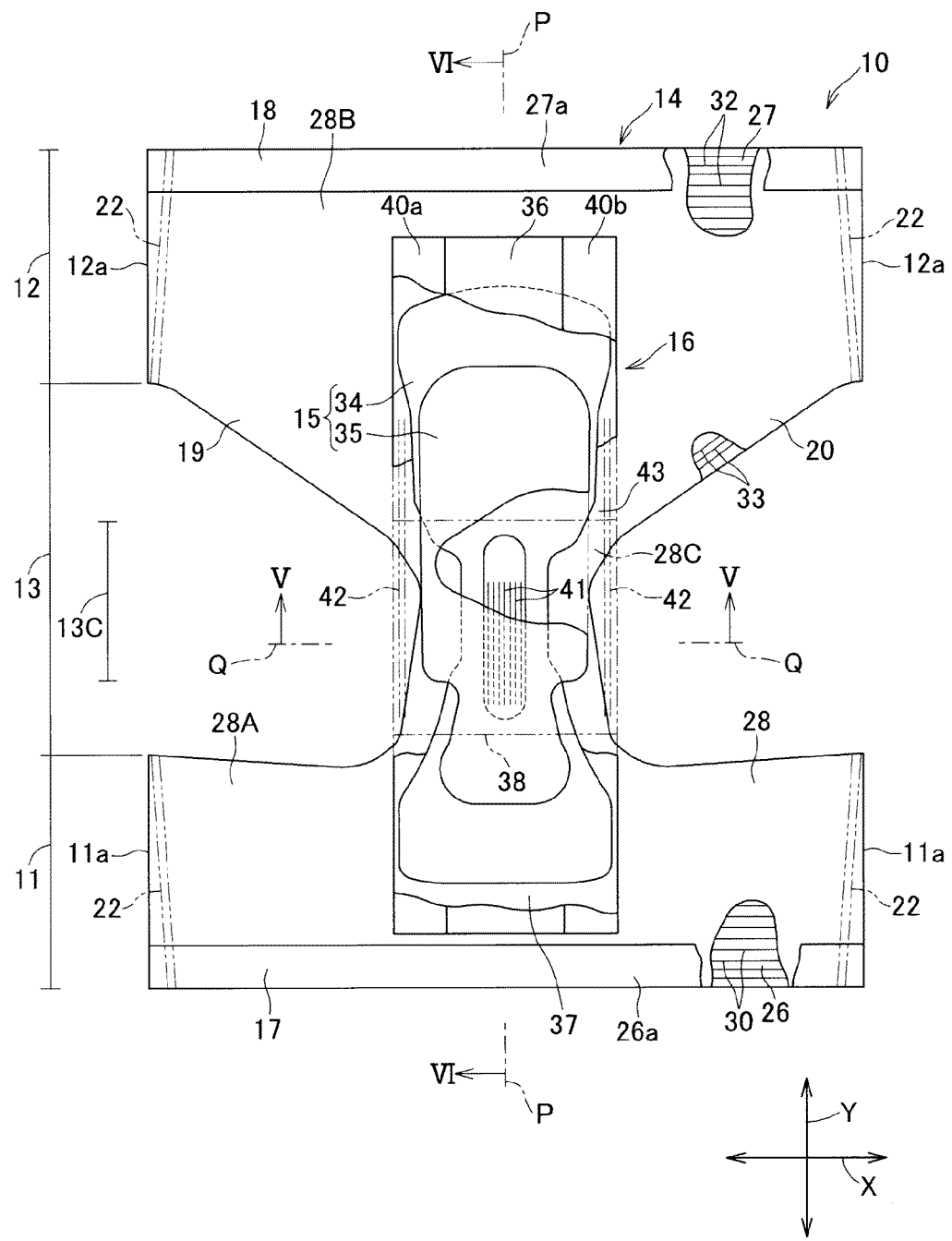
FIG. 2 is a partially cutaway plan view showing the diaper flatly developed as viewed from a skin-facing side.
Figure 3:
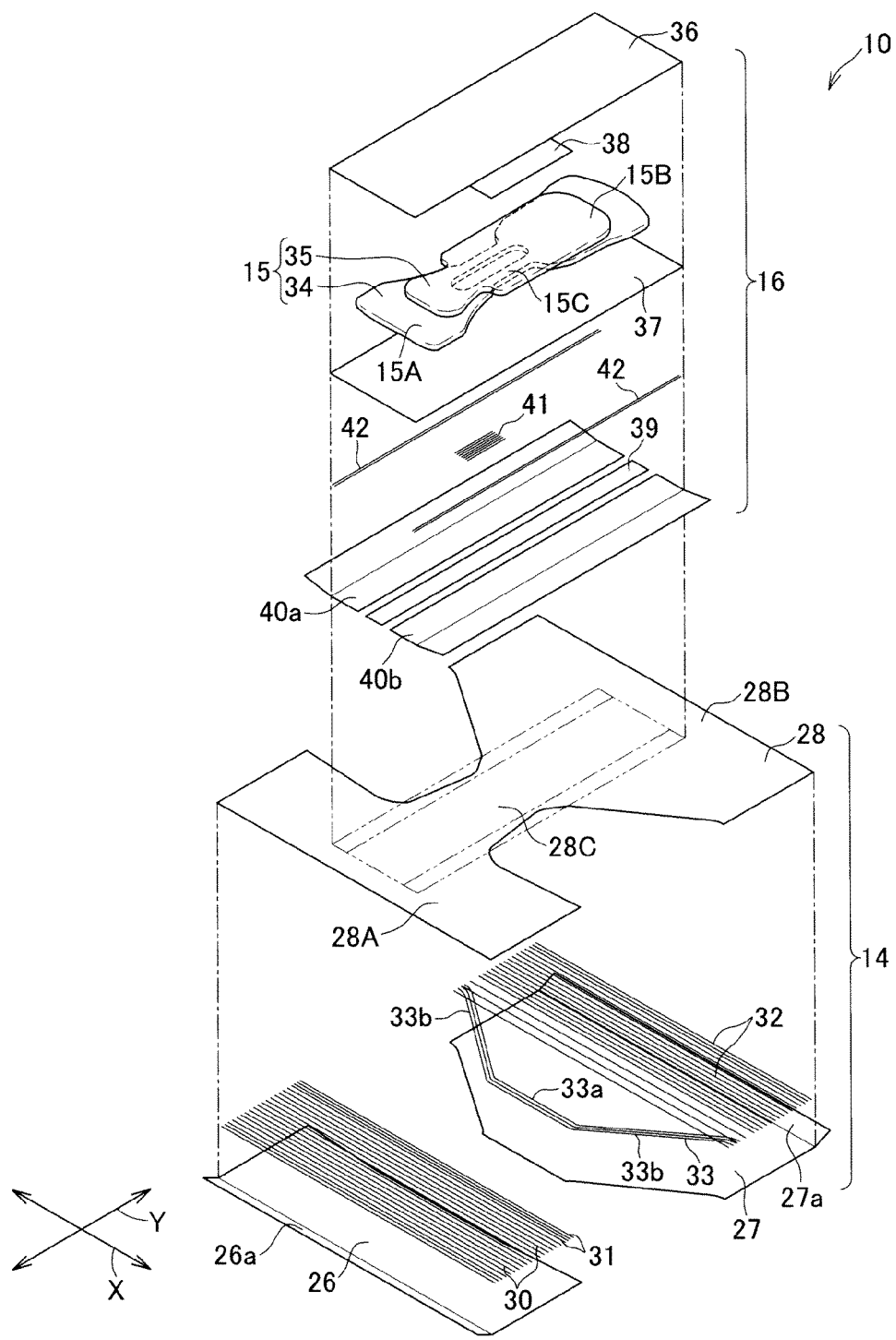
FIG. 3 is an exploded perspective view of the diaper.

Referring to FIGS. 1 through 3, the diaper 10 having a longitudinal direction Y being parallel to a longitudinal axis P, a transverse direction X being orthogonal to the longitudinal direction Y and in parallel to a transverse axis Q, includes a chassis 14 and a liquid absorbent structure 16, and further includes a skin-facing side, a non-skin-facing side, a front waist region (front region) 11, a rear waist region (rear region) 12 and a crotch region 13 extending between the front and rear waist regions 11, 12, and a liquid absorbent structure 16 provided on the skin-facing side of the chassis 14 and including an absorbent layer 15 extending across the crotch region 13 into the front and rear waist regions 11, 12.

The diaper 10 is contoured by front and rear ends 17, 18 opposite to each other in the longitudinal direction Y and side edges 19, 20 opposite to each other in the transverse direction X. The opposite side edges 19, 20 are curved inward so that the respective side edges 19, 20 may be put in close contact with the wearer's thighs with a desired fit when the diaper 10 is put on the wearer's body. Consequentially, a width dimension of the crotch region 13 in its midsection 13C is smaller than those of the front and rear waist regions 11, 12. Opposite side edges 11a of the front waist region 11 and opposite side edges 12a of the rear waist region 12 are coupled along a series of side seams arranged in the longitudinal direction Y and thereby a waist-opening 23 and a pair of leg-openings 24 are defined. The side seams 22 are formed of thermal or ultrasonic debossing techniques.

The chassis 14 includes a front outer sheet 26 defining the outer surface of the front waist region 11, a rear outer sheet 27 defining the outer surface of the rear waist region 12 and an inner sheet 28 lying on the sides of the front and rear outer sheets 26, 27 facing the wearer's skin. The inner sheet 28 includes a front section 28A having substantially the same shape as the front outer sheet 26 and overlapping the front outer sheet 26, a rear section 28B having substantially the same shape as the rear outer sheet 27 and overlapping the rear outer sheet 27, and a midsection 28C extending between the front and rear sections 28A, 28B and concavely constricted so as to have a width dimension smaller than those of the front and rear sections 28A, 28B.

Two or more thread-, strand- or string-like front waist elastic element 30 and two or more thread-, strand- or string-like front leg elastic members 31 extending in the transverse direction X are secured in a contractible manner between the front outer sheet 26 and the front section 28A of the inner sheet 28. In a similar fashion, two or more thread-, strand- or string-like rear waist elastic elements 32 and two or more thread-, strand- or string-like rear side leg elastic members 33 extending in the transverse direction X are secured in a contractible manner between the rear outer sheet 27 and the rear section 28B of the inner sheet 28. A front end 26a of the front outer sheet 26 and a rear end 27a of the rear outer sheet 27 are folded along respective fold lines extending in the transverse direction X so as to be bonded to the skin-facing side of the inner sheet 28 with hot melt adhesives.

The front and rear outer sheets 26, 27 are bonded to the inner sheet 28 with hot melt adhesives intermittently applied at least to inner surfaces of the front and rear outer sheets 26, 27 or to an inner surface of the inner sheet 28. It is also possible to bond the front and rear outer sheets 26, 27 to the inner sheet 28 only with hot melt adhesives applied to respective full peripheral surfaces of the front and rear waist elastic elements 30, 32.

As materials for the front and rear outer sheets 26, 27 and the inner sheet 28, for example, leak-barrier and moisture-permeable plastic films, nonwoven fabrics of hydrophobic fibers or laminate sheets thereof may be used. Examples of the nonwoven fabrics useful for this purpose include air-through nonwoven fabrics, spunbonded nonwoven fabrics and point-bonded nonwoven fabrics each having a basis mass in a range of about 10 to about 30 $g/m^2$, more preferably in a range of about 15 to about 20 $g/m^2$.

As materials for the front waist elastic element 30, two or more thread-, strand- or string-like elastic members each having a fineness in a range of about 600 to 980 dtex and a stretch ratio preferably in a range of about 2.5 to 4.0 may be used. These elastic members are arranged to be spaced one from another by a predetermined distance in the longitudinal direction Y of the diaper 10. As materials for the front leg elastic elements 31, thread-, strand- or string-like two or more elastic members extending in the transverse direction X from the lower end of the front waist region 11 may be used. Each of these elastic members has a fineness in a range of about 600 to about 800 dtex and a stretch ratio in a range of about 1.5 to about 3.5.

As materials for the rear waist elastic element 32, two or more thread-, strand- or string-like elastic members each having a fineness in a range of about 600 to about 980 dtex and a stretch ratio preferably in a range of about 2.5 to about 4.0 may be used. These elastic members are arranged to be spaced one from another by a predetermined distance in the longitudinal direction Y of the diaper 10. As the rear leg elastic element 33, thread-, string- or strand-like three elastic members each having a fineness in a range of about 600 to about 800 dtex may be used. These three elastic members extend along the lower end of the rear waist region 12 so as to be curved toward the transverse axis Q. Each of the rear side leg elastic members 33 includes a rectilinear segment 33a overlapping the liquid absorbent structure 16 and a pair of sloping segments 33b extending from the side edges of the rear waist region 12 to respective ends of the rectilinear segment 33a. The rectilinear segment 33a has a stretch ratio in a range of about 0.5 to about 2.0 and each of the sloping segments 33b has a stretch ratio preferably in a range of about 1.5 to about 3.0. The rear side leg elastic members 33 partially intersect with the liquid absorbent structure 16 in this manner and, in consequence, a tensile stress of these elastic members 33 ensures the liquid absorbent structure 16 to be kept in close contact with the wearer's body. The stretch ratio of the rectilinear segment 33a is lower than that of the sloping segment 33b and therefore the tensile stress of the rectilinear segment 33a is unlikely to cause wrinkles in the absorbent layer 15 and thereby deteriorate the absorption performance of the absorbent layer 15. As will be apparent from FIG. 1, the front and rear waist regions 11, 12 are formed with a plurality of fine wrinkles under the effect of the front and rear waist elastic elements 30, 32 provided in these waist regions, respectively.

The liquid absorbent structure 16 includes the absorbent layer 15 in the form of a vertically two-layered structure defined by first and second absorbent cores 34, 35, a bodyside liner 36 lying on the upper surface of the absorbent layer 15 and a poorly liquid permeable or liquid impermeable backsheet 37 lying on the lower surface of the absorbent layer 15. An interlayer sheet 38 to be described later is optionally interposed between the bodyside liner 36 and the absorbent layer 15. The absorbent layer 15 includes a front end section 15A lying on the side of the front waist region 11, a rear section 15B lying on the side of the rear waist region 12 and an intermediate section 15C lying between the front and rear end section 15A, 15B. Depending on particular sizes of the diaper 10, the front region 15A and the rear region 15B of the absorbent layer 15 may lie in the front waist region 11 and the rear waist region 12, respectively, and, in an extreme case, the absorbent layer 15 as a whole may lie only in the crotch region 13.

The liquid absorbent structure 16 is attached to the side (skin-facing side) of the inner sheet 28 facing the wearer's skin with hot melt adhesive and further includes a cover sheet 39 centrally extending in the longitudinal direction Y and serving to secure elastic members and a pair of leakage-barrier sheets 40a, 40b extending on both sides of the cover sheet 39. A crotch elastic element 41 including two or more thread-, strand- or string-like elastic members extending in the longitudinal direction Y is interposed between the backsheet 37 and the cover sheet 39.

The respective leakage-barrier sheets 40a, 40b are provided with respective leg elastic elements 42 each including two or more thread-, string- or strand-like elastic members. The respective leg elastic elements 42 are secured within associated sleeves 43 formed of folding the respective leakage-barrier sheets 40a, 40b. With the diaper 10 put on the wearer's body, the sleeves 43 are put in close contact with the wearer's thighs and function as gasket cuffs to help prevent bodily waste from leaking sideways.

The first and second absorbent cores 34, 35 are respectively formed from a mass of absorptive materials, for example, absorbent fibers such as fluff wood pulp having a basis mass in a range of about 100 to about 500 g/m² and/or a mass of superabsorbent polymer particles (SAP) having a basis mass in a range of about 0 to about 500 g/m² and, thermoplastic synthetic fibers (staple fibers) having a basis mass in a range of about 10 to about 30 g/m² optionally mixed with the above-mentioned mass or masses. The absorbent layer 15 may be wrapped with tissue paper having a diffusion property in order to improve a shape retention performance and a bodily fluid diffusion property of the absorbent core.

The bodyside liner 36 may be formed, for example, of nonwoven fabrics of hydrophilic fibers or hydrophobic fibers treated to become hydrophilic, perforated plastic films, or laminate sheets thereof. The nonwoven fabrics suitable for this purpose includes an air-through nonwoven fabrics, spunbonded nonwoven fabrics and spunbond/meltblown/spunbond (SMS) nonwoven fabrics each having a basis mass in a range of about 20 to about 50 g/m², more preferably in a range of about 20 to about 35 g/m².

The backsheets 37 may be formed, for example, of plastic films, hydrophobic fiber nonwoven fabrics or laminate sheets thereof. In plastic films used to form the backsheet 37, for example, moisture-permeable polyethylene films having a basis mass in a range of about 17 to about 25 g/m² or moisture-permeable polyethylene films having a basis mass in a range of about 15 to about 25 g/m² may be used.

Both the bodyside liner 36 and the backsheet 37 extend outward beyond the peripheral edge of the absorbent layer 15 and are bonded to each other outside the peripheral edge of the absorbent layer 15 with hot melt adhesives applied in a spiral pattern at least to respective inner surfaces of the bodyside liner 36 and backsheet 37 at a basis mass in a range of about 4 to about 10 g/m².

The interlayer sheet 38 may be formed, for example, of hydrophilic nonwoven fabrics, preferably nonwoven fabrics providing cushioning properties higher than that provided by the bodyside liner 36. The interlayer sheet 38 has its length dimension in the longitudinal direction Y smaller than that of the bodyside liner 36 and may be formed of sheet members substantially similar to the bodyside liner 36. The interlayer sheet 38 interposed between the bodyside liner 36 and the absorbent layer 15 serves to accelerate diffusion of bodily fluids, thereby to accelerate absorption of bodily fluids and to help prevent backflow of bodily fluids.

The leakage-barrier sheets 40a, 40b may be formed, for example, of leak-barrier and moisture-permeable plastic films, hydrophobic nonwoven fabrics or laminate sheets thereof. The nonwoven fabrics suitable for this purpose includes SMS nonwoven fabrics and spunbonded nonwoven fabrics each having a basis mass in a range of about 10 to about 30 g/m², more preferably in a range of about 12 to about 18 g/m². The plastic films suitable for this purpose includes moisture-permeable polyethylene films having a basis mass in a range of about 17 to about 25 g/m² and a moisture-permeable polyethylene films having a basis mass in a range of about 15 to about 25 g/m².

As the material for the respective leg elastic elements 42, thread-, strand- or string-like elastic members each having a thickness in a range of about 500 to about 900 dtex and preferred stretch ratio in a range of about 2.5 to about 4.0 may be used. The crotch elastic elements 41 may be formed of a plurality of thread-, strand- or string-like elastic members each having a thickness in a range of about 400 to about 900 dtex and stretch ratio in a range of about 1.8 to about 2.5 wherein two similar elastic members respectively located on both sides have a stretch ratio preferably in a range of about 1.4 to about 2.0 and a plurality of middle elastic members have a stretch ratio preferably in a range of about 1.8 to about 2.5. It is also possible to form both the crotch elastic elements 41 and the respective leg elastic elements 42 not of two or more elastic members but of ribbon-like elastic sheets, respectively, each having a predetermined width dimension.

Figure 4:
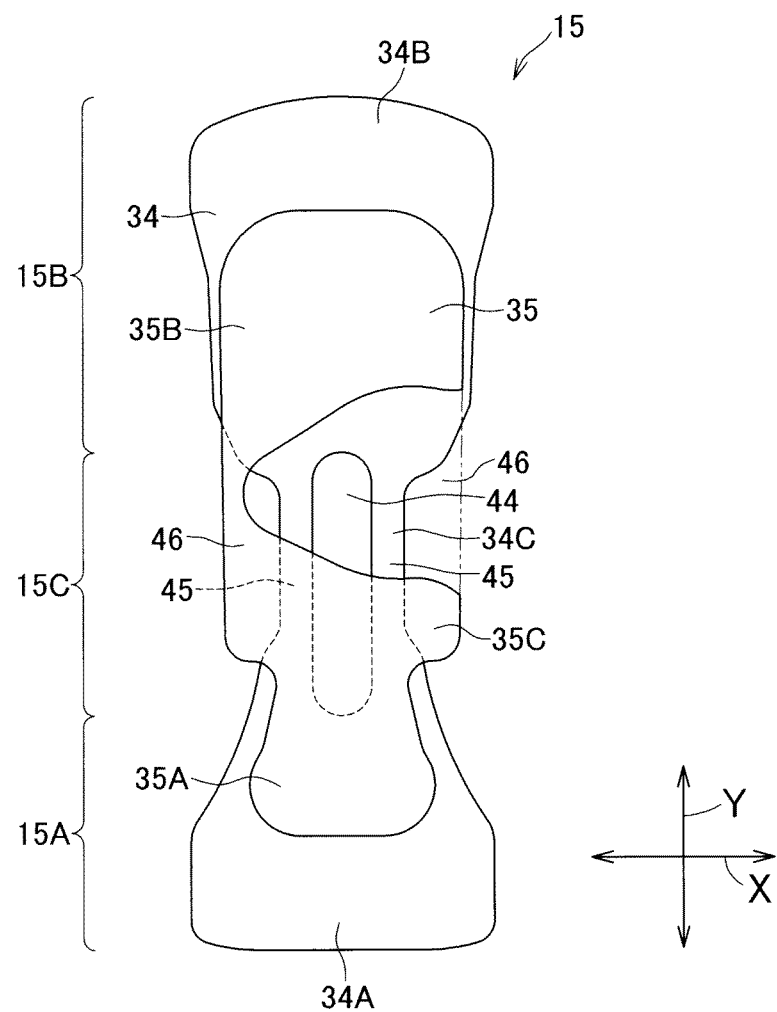
FIG. 4 is a partially cutaway plan view of an absorbent layer.

Referring to FIG. 4, the first absorbent core 34 defining the lower layer includes a front region 34A extending from the front side of the crotch region 13 into the front waist region 11, a rear region 34B extending from the rear side of the crotch region 13 into the rear waist region 13 and an intermediate region 34C extending in the longitudinal direction Y between the front and rear regions 34A, 34B and having a width dimension narrower than those of the front and rear regions 34A, 34B. The second absorbent core 35 defining the upper layer includes a rear region 35B lying on the side of the rear waist region 12, a front region 35A lying on the side of the front waist region 11 and having a width dimension narrower than that of the rear region 35B and an intermediate region 35C extending between the front and rear regions 35A, 35B. The intermediate section 34C of the first absorbent core 34 is formed with a central depression 44 extending in the longitudinal direction Y and width-restricted regions 45 extending on both sides of the central depression 44.

The first and second absorbent cores 34, 35 lie one upon another wherein a length dimension of the second absorbent core 35 in the longitudinal direction Y is smaller than that of the first absorbent core 34 and the front and rear regions 34A, 34B of the first absorbent core 34 extend outward partially beyond the front and rear regions 35A, 35B of the second absorbent core 35. In the intermediate section 13C of the crotch region 13, the second absorbent core 35 extends outward in the transverse direction X partially beyond the intermediate section 34C of the first absorbent core 34 so as to define lateral extensions 46. The portion of the first absorbent core 34 formed with the central depression 44 contains none of the absorbent material for the first absorbent core 34 and, if contains, its basis mass is lower than that in the remaining portion of the first absorbent core 34. Consequently, the first absorbent core 34 is easily folded along this central depression 44.

The central depression 44 may be formed in both the first absorbent core 34 and the second absorbent core 35, or in at least one of the first and second absorbent cores 34, 35. Further, the central depression 44 may have the form of a slit, or several slits, extending through the core in its thickness direction.

Figure 5:
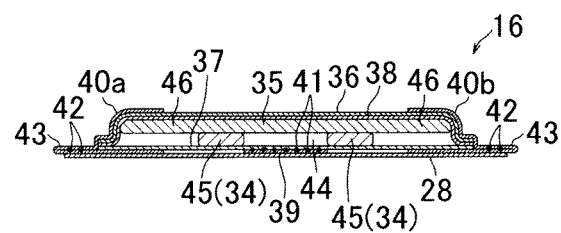
FIG. 5 is a sectional view taken along line V-V in FIG. 2.
Figure 6:
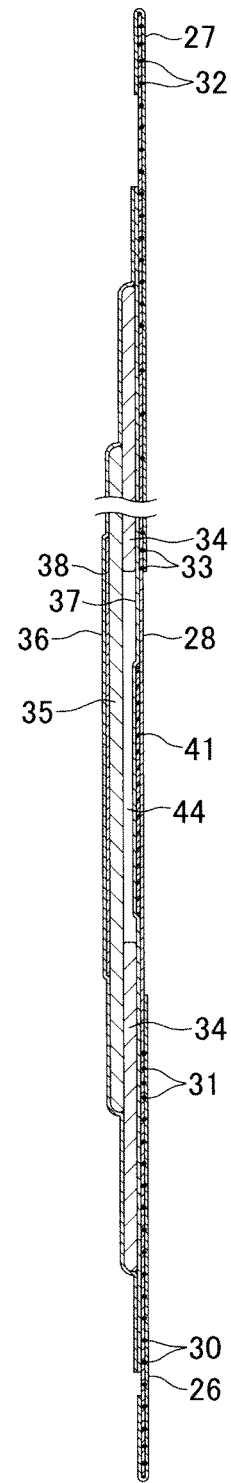
FIG. 6 is a sectional view taken along line VI-VI in FIG. 2.
Figure 7:
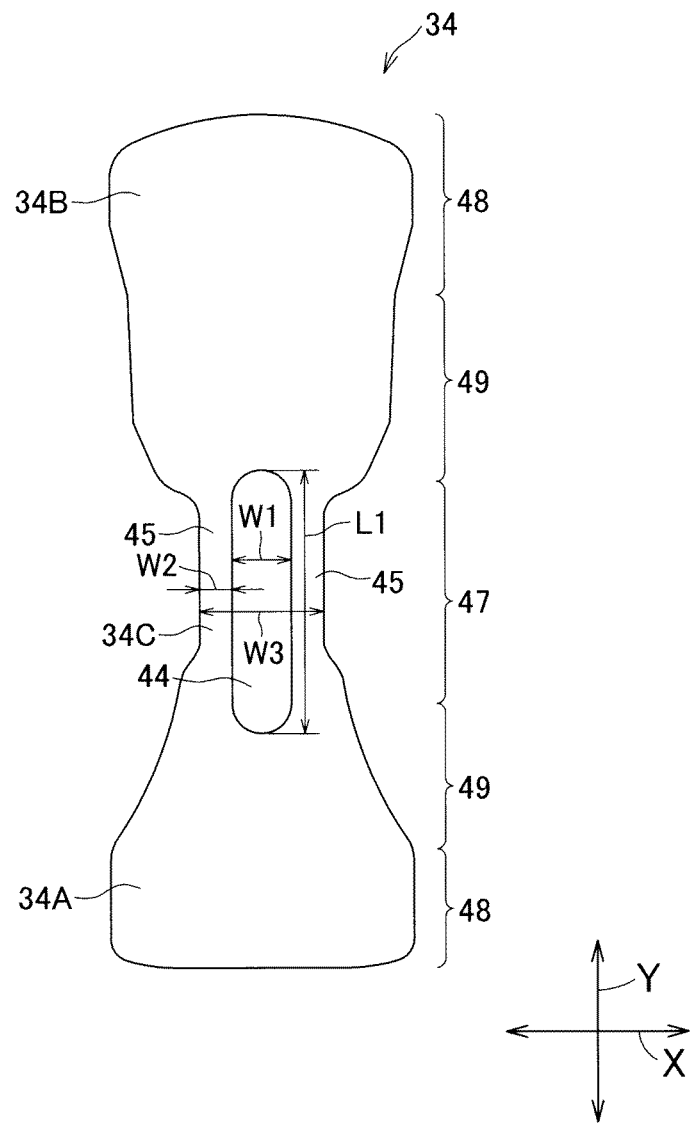
FIG. 7 is a plan view of a first absorbent core.

Referring to FIGS. 2, 5 and 7, the crotch elastic element 41 is located so as to overlap the central depression 44 of the first absorbent core 34. With such an arrangement, the intermediate section 35C of the second absorbent core 35 can be kept in close contact with the wearer's body under the effect of contractile force of the crotch elastic element 41 and thereby it is assured that bodily fluids can be quickly absorbed by the second absorbent core 35. In addition, in the intermediate section 13C of the crotch region 13, the leg elastic elements 42 are provided in the vicinities of the respective lateral extensions 46 of the second absorbent core 35. These lateral extensions 46 of the second absorbent core 35 raise themselves together with the gasket cuffs defined by the respective sleeves 43 so that the intermediate section 13C of the crotch region 13 may be curved along the wearer's body with sufficiently high fit to prevent bodily fluids from leaking sideways. Not only in the present embodiment but also in other embodiments (including those in which the absorbent core is of a monolayer construction), it is preferred that the crotch elastic element 41 is located so as to at least partially overlap the central depression 44.

Referring to FIG. 7, the first absorbent core 34 includes a high density zone 47 defined in the narrow width regions 45 of the intermediate section 34C and outside the central depression 44, low density zones 48 defined in the front and rear sections 34A, 34B, and moderate density zones 49 each defined between the high density zone 47 and the associated low density zone 48. Of these zones, the high density zone 47 has the highest density and the moderate density zone 49 has density higher than that of the low density zone 48. The correlative relationship of the density levels in these zones may be represented as follows: The high density zone 47> the moderate density zones 49> the low density zones 48.

The density of the first absorbent core 34 varies so as to be in a range of about 0.2 to about 0.6 g/cm$^3$ in the high density zone 47, in a range of about 0.13 to about 0.27 g/cm$^3$ in the respective moderate density zones 49, and in a range of about 0.1 to about 0.2 g/cm$^3$ in the respective low density zones 48. Now assuming that the mixture of fluff wood pulp having a basis mass of about 250 g/m$^2$ and superabsorbent polymer particles having a basis mass of about 150 g/m$^2$ is used as the first absorbent core 34, thickness dimension of this first absorbent core 34 is in a range of about 0.5 to about 2.3 mm, more preferably in a range of about 0.8 to about 2.0 mm in the high density zone 47, in a range of about 1.2 to about 3.1 mm, more preferably in a range of about 1.5 to about 2.8 mm in the respective moderate density zones 49, and in a range of about 1.6 to about 4.0 mm, more preferably in a range of about 2.0 to about 3.6 mm in the respective low density zones 48. The density of the high density zone 47 is six times or less, preferably three times or less of the density in the respective low density zones 48.

<Measuring Method for Thickness Dimension of the First Absorbent Core 34>

The thickness dimensions of the first absorbent core 34 in the high density zone 47, the moderate density zones 49 and the low density zones 48 were measured using a thickness meter (PEACOCK DIGITAL THICKNESS GAUGE JA-257 manufactured by OZAKI MFG CO. LTD.). Specifically, the first absorbent core 34 was detached from the diaper 10 and cut into the respective zones to obtain test pieces. Measurement was conducted on these test pieces under a load of 10 gf/cm$^2$.

<Density Measurement for the First Absorbent Core>

The first absorbent core 34 was detached from the diaper 10 and cut into the respective zones 47, 48, 49 and thickness (mm) was measured for the respective zones using the above-mentioned thickness measuring method. Now the respective zones for thickness measurement were cut in a size of about 2.0 cm in the longitudinal direction Y×about 2.0 cm in the transverse direction X to obtain test pieces and mass (g) of them were weighed. The respective measurement values were substituted into a formula: density (g/cm$^3$)=mass (g)/thickness dimension (mm)/area (cm$^2$)×10 to calculate densities of the respective zones 47, 48, 49. The sign "/" means "devided by."

The first absorbent core 34 is formed from absorbent fibers having a basis mass in a range of about 100 to about 500 g/m$^2$ and superabsorbent polymer particles having a basis mass in a range of about 0 to about 500 g/m$^3$ into a pre-formed first absorbent core having a substantially uniform thickness as a whole. The pre-formed first absorbent core is subsequently press-worked in a process as will be described later in details to form the above-mentioned zones differentiated one from another in density and stiffness. Specifically, the pre-formed first absorbent core may be evenly pressed by a pair of press rollers to reduce, either gradually or stepwise, the density from the most narrow width regions 45 toward the front and rear sections 34A, 34B. In this way, the pre-formed first absorbent core having a substantially uniform thickness may be press-worked to define the zones differentiated in density and stiffness in the first absorbent core 34. In order to pre-form the high density zone 47 with the width dimension of the intermediate section 34C in the first absorbent core 34 to be smaller than those of the front and rear sections 34A, 34B, the narrow width regions 45 in the intermediate section 34C preferably has a width dimension W2 in the transverse direction X corresponding to about 20% or less, more preferably about 13% or less of a width dimension of the front and rear section 34A, 34B (i.e., the low density zones 48) in the transverse direction X. While the width dimension of the front and rear sections 34A, 34B may be gradually reduced to achieve gradual variation of density and stiffness according to the present embodiment, an alternative embodiment is also possible as long as the intermediate section 35C is formed with the high density zone 47. For example, the intermediate section 34C having substantially the same width dimension as those of the front and rear sections 34A, 34B may be formed with the central depression 44 to form the narrow width region 45 with the high density zone 47.

Figure 8:
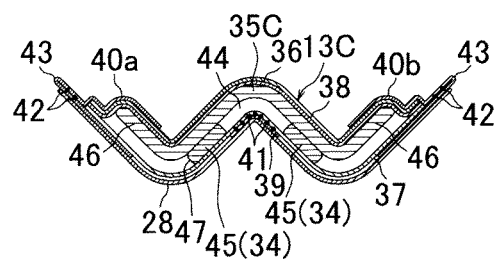
FIG. 8 is a sectional view similar to FIG. 5, with the diaper put on the wearer's body.

Referring to FIG. 8, the high density zone 47 formed in the narrow width region 45 of first absorbent core 34 facilitates the intermediate section 13 of the crotch region 13 to be regularly folded substantially in a W-shape as viewed in the cross-section and thereby to assure that the intermediate section 35C of the second absorbent core 35 is kept in close contact with the wearer's body. As has previously been described, the central depression 44 and the crotch elastic elements 41 formed and attached, respectively, in the intermediate section 34C of the first absorbent core 34 are adapted to facilitate the intermediate section 35C of the second absorbent core 35 to be convexly curved toward the wearer's body. However, if the stiffness of the narrow width region 45 of the first absorbent core 34 is relatively low, the intermediate section 13c of the crotch region 13 might be compressed between the wearer's thighs and, in consequence, the narrow width region 45 might be twisted and the crotch region 13 might be irregularly folded. Consequently, the intermediate section 35C of the second absorbent core 35 could not be convexly curved sufficiently toward the wearer's body.

In the present embodiment, however, the narrow width region 45 of the first absorbent core 34 is formed with the high density zone 47, so that the narrow width region 45 is unlikely to be twisted. The high density zone 47 functions as a proximal point around which the intermediate section 35C of the second absorbent core 35 is curved along the wearer's body. More specifically, the lateral extensions 46 of the second absorbent core 35 raise themselves under contraction of the leg elastic elements 42 and the crotch region 13 is folded along both transverse sides of the narrow width region 45. In this way, it is assured that the intermediate section 35C of the second absorbent layer 35 is regularly and convexly curved toward the wearer's body. If the first absorbent core 34 as a whole has a stiffness equal to that of the high density zone 47, the front and rear end section 15A, 15B of the absorbent layer 15 would become relatively hard and, in consequence, these sections 15A, 15B might be spaced apart from the wearer's body and/or might create a discomfort feeling against the wearer. However, in the present embodiment, the front and rear sections 34A, 34B of the first absorbent core 34 are formed with the low density zones 48, so that the front and rear end section 15A, 15B of the first and second absorbent cores 34, 35 may each have a desired flexibility, and thereby the above-mentioned disadvantageous possibility may be reliably eliminated.

If the high density zone 47 and the low density zones 48 are directly adjacent each other in the first absorbent core 34, the stiffness value would drastically change and wrinkles extending in the transverse direction X would be developed in the vicinities of the boundaries of these adjacent zones 48. Consequently, there is a possibility that the crotch region 13 might be irregularly folded. In the present embodiment, however, the stiffness of the first absorbent core 34 is reduced, either gradually or stepwise, from the intermediate section 34C being formed with the high density zone 47 toward the front and rear sections 34A, 34B, and the moderate density zones 49 are formed between the high density zone 47 and the low density zones 48, so that the stiffness value may vary as gently as possible and the above-mentioned disadvantageous possibility may be further reliably eliminated.

Referring again to FIG. 7, various exemplary dimensions of the first absorbent core 34 will be specified. The central depression 44 in the intermediate section 34C has a width dimension W1 in the transverse direction X in a range of about 3 to about 50 mm, preferably in a range of about 25 to about 50 mm, and a length dimension L1 in the longitudinal direction Y in a range of about 100 to about 200 mm. The high density zone 47 is defined on both sides of the central depression 44 and therefore its length dimension in the longitudinal direction Y is equal to that of the central depression 44 but its width dimension W2 in the transverse direction X is in a range of about 5 to about 60 mm, preferably in a range of about 10 to about 40 mm. The intermediate section 35C of the first absorbent core 34 has a width dimension W3 in the transverse direction X in a range of about 45 to about 130 mm. If the length dimension of the central depression 44 in the longitudinal direction Y is less than about 100 mm, it may be difficult to curve the intermediate section 35C of the second absorbent core 35 convexly toward the wearer's skin, and also the high density zone 47 may not sufficiently function as fold guiding means along which the first absorbent core 34 is to be folded. Although the width dimension W2 of the narrow width region 45 may be as low as 5 mm, if W2 is less than about 10 mm in some specific configurations, the high density zone 47 may not sufficiently function as the fold guiding means. Likewise, although the width dimension W2 of the narrow width region 45 may be as high as 60 mm, if this width dimension W2 is larger than about 40 mm in some specific configurations, a relatively wide range of the absorbent layer 15 may not follow movements of the wearer's body and eventually may create a discomfort feeling against the wearer.

While the absorbent layer 15 is provided in the form of a bilayer structure including the first absorbent core 34 and the second absorbent core 35 according to the present embodiment, it is possible to form the absorbent layer 15 only of the first absorbent core 34 or by more than two absorbent cores as long as the crotch region 13 can be folded substantially in a W-shape in a regular way. It is possible to dimension the outer shape of the second absorbent core 35 to be larger than that of the first absorbent core 34. It is also possible to arrange so that the first absorbent core 34 defines the upper layer and the second absorbent layer 35 defines the lower layer. Furthermore, it is also possible to form the first central depression 44 of the first absorbent core 34 as a pair of grooves arranged symmetrically about the longitudinal axis P.

Figure 9:
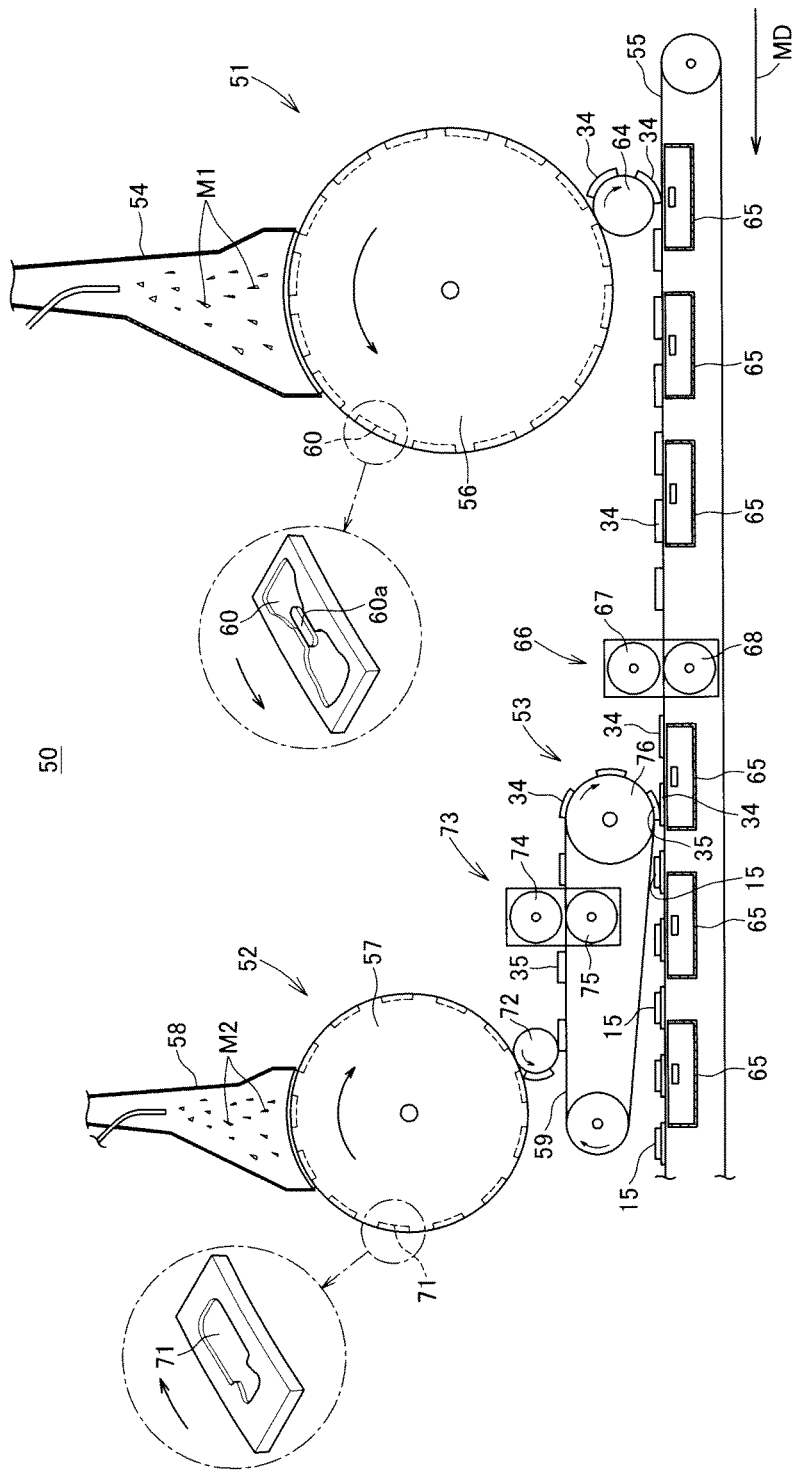
FIG. 9 is a diagram schematically illustrating an apparatus for making an absorbent layer.

FIG. 9 is a schematic diagram illustrating an apparatus 50 according to the present embodiment for making the above-described absorbent layer 15. The apparatus 50 includes a first molding station 51 to mold the first absorbent core 34 from absorptive materials (M1), for example, one of fluff wood pulp and superabsorbent polymer particles or a mixture thereof, a second molding station 52 to mold the second absorbent core 35 from the above-mentioned (or a different) absorptive materials, and a laminating station 53 to laminate the first absorbent core 34 and the second absorbent core 35 together. The first molding station 51 includes, in turn, a first rotary suction drum 56, a feed unit (not illustrated) provided with a feed conduit 54 for the above-mentioned absorptive materials (M1) located so as to cover a part of the first rotary suction drum 56 and a first conveyor belt (first conveying means) 55 underlying the first rotary suction drum 56. The second molding station 52 includes, in turn, a second rotary suction drum 57, a feed unit (not illustrated) provided with a feed conduit 58 for the above-mentioned absorptive material (M2) located so as to cover a part of the second rotary suction drum 57 and a second conveyor belt (second conveying means) 59 underlying the second rotary suction drum 57. As viewed in the machine direction MD, the second conveyor belt 59 runs in a direction opposite to the direction in which the first conveyor belt 55 runs. As will be described later, the first absorbent core 34 is press-worked at a first press station (press-working station) 66, and then the second absorbent core 35 is press-worked at a second press station (press-working station) 73. The feed conduits 54, 58 respectively provided at the first and second molding stations 51, 52 include, in addition to the feed conduits for the above-mentioned absorptive materials (M1), (M2) such as fluff wood pulp, fine pipes serving to feed superabsorbent polymer particles and means serving to mix (air blasting means) the superabsorbent polymer particles into the absorptive materials.

The operation is started at the first molding station 51. The above-mentioned absorptive materials (M1) are fed through the feed conduit 54 toward the first rotary suction drum 56 and successively deposited in substantially hourglass-shaped recessed molds 60 formed on an outer peripheral surface of the first rotary suction drum 56 at regular intervals. In this manner, the first absorbent cores 34 are shaped (pre-formed). Each of the recessed molds 60 is formed in its central region with a protrusion 60a which is relatively long in a longitudinal direction of the recessed molds 60 and none or almost (substantially) none of the above-mentioned absorptive materials are deposited in a region of the recessed mold defined by the protrusion 60a and, as a result, each of the first absorbent core 34 is pre-formed in its region corresponding to the protrusion 60a with the central depression 44 as illustrated in FIG. 10.

Then, these pre-formed first absorbent cores 34 are successively transferred by means of a delivery suction roller (third conveying means) 64 underlying the first rotary suction drum 56 and rotating in a direction opposite to a rotating direction of the first rotary suction drum 56 onto the mesh-like first conveyor belt (first conveying means) 55 running at a conveyance velocity in a range of about 60 to about 130 m/min and conveyed in the machine direction MD. The recessed molds 60 formed on the outer peripheral surface of the first rotary suction drum 56 respectively have mesh bottoms so that the recessed molds 60 and the delivery suction roller 64 may be subjected to a negative pressure by a suction unit (not illustrated) and thereby the pre-formed first absorbent core 34 may be protected from losing their desired shapes and the above-mentioned absorptive materials may be prevented from flying apart. Below the first conveyor belt 55, a plurality of suction boxes 65 are located so that the pre-formed first absorbent cores 34 loaded on the conveyor belt 55 may be transported in the machine direction MD in a shape retained state. The respective recessed molds 60 formed on the outer peripheral surface of the first rotary suction drum 56 are substantially uniform in the total height as well as in the depth thereof and correspondingly the pre-formed first absorbent cores 34 transferred onto the first conveyor belt 55 also are substantially uniform (except in the central depressions 44 corresponding to the protrusions 60a) in the mass per unit area (basis mass) as well as in the thickness thereof.

Now at the first press station 66, the pre-formed first absorbent cores 34 on the first conveyor belt 55 are successively guided into a clearance between a first press roller 67 having a predetermined curvature factor and a first anvil roller 68 opposed to the first press roller 67 so as to be compressed between these two rollers 67, 68. The first press roller 67 is installed so as to exert a predetermined force on a rotary shaft of the first anvil roller 68.

Figure 10:
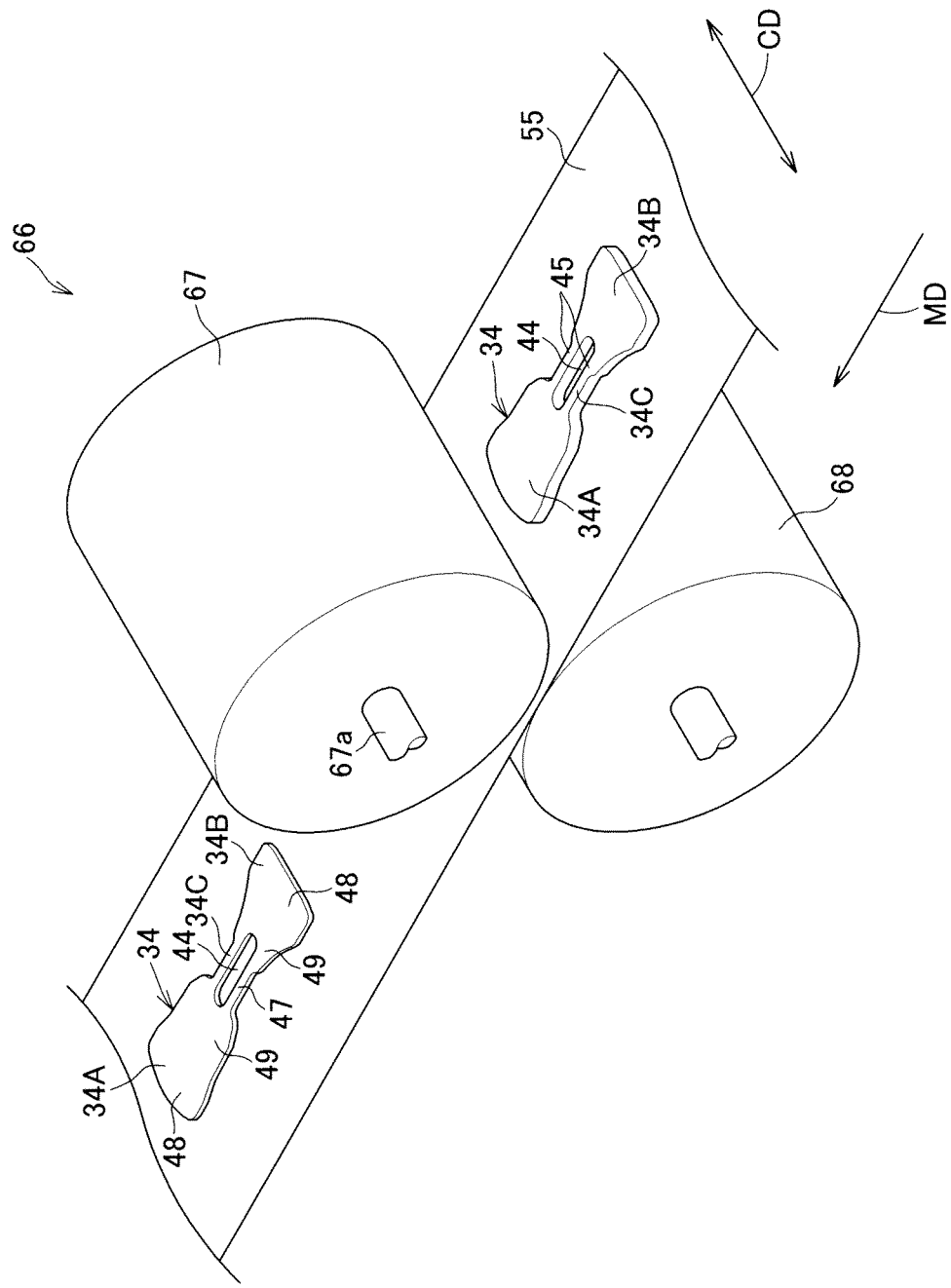
FIG. 10 is a perspective view illustrating a first press station of the apparatus.

Referring to FIG. 10, the first press roller 67 is installed so that its own weight and a cylinder (not illustrated) attached thereto may exert a predetermined force to the pre-formed first absorbent cores 34 being successively guided into a clearance defined between the first press roller 67 and the first anvil roller 68. As has previously been described, each of the pre-formed first absorbent cores 34 immediately before being press-worked at the first press station 66 has the substantially hourglass-like shape, the substantially uniform thickness, the substantially uniform mass per unit area, and the central depression 44.

Such pre-formed first absorbent core 34 may be press-worked at the first press station 66 to form the intermediate section with the width-restricted region 45 having a thickness dimension smaller than in the remaining sections and density as well as stiffness higher than those of the remaining sections for the reason that the width-restricted region 45 is subjected to the highest pressure. Specifically, the first press roller 67 and the first anvil roller 68 have respective diameter in a range of about 250 to about 350 mm and respective width dimension in the cross direction CD in a range of about 400 to about 500 mm. The first press roller 67 and the first anvil roller 68 are spaced from each other by a distance in a range of about 0.5 to about 1.2 mm and opposed to each other. The pre-formed first absorbent core 34 having a thickness dimension in a range of about 1.0 to about 5.0 mm may be guided through the clearance defined between the first press roller 67 and the first anvil roller 68 so as to be compressed between these rollers 67, 68 to subject the respective regions of the pre-formed first absorbent core 34 extending in the cross direction CD to a linear pressure of a predetermined width. A length dimension of the linearly pressurized region (length dimension of the linear pressure in the machine direction MD) is smaller than a length dimension in the machine direction MD of at least the most narrow width region 45 of the intermediate section 34C of the pre-formed first absorbent core 34. The pressure exerted on the pre-formed first absorbent core 34 depends on the area of the pre-formed first absorbent core 34 to be pressurized. In other words, the highest force is exerted on the region having the smallest area. Since the pre-formed first absorbent core 34 is shaped so that its width dimension gradually increases from the most narrow width region 45 toward the front and rear sections 34A, 34B, density as well as stiffness of the first absorbent core 34 having been press-worked gradually decreases from the intermediate section 34C toward the front and rear sections 34A, 34B and a thickness dimension thereof gradually increases from the intermediate section 34C toward the front and rear sections 34A, 34B. In consequence, the first absorbent core 34 having been press-worked in the first press-working step 66 is formed with the high density zone 47, the moderate density zones 49 and the low density zones 48 respectively having density values and stiffness values differentiated depending on the zones. The press-working does not significantly change the mass per unit area of the first absorbent cores 34. Therefore, the first absorbent core 34 in the final product still includes the substantially uniform mass per unit area over an entirety of the first absorbent cores 34 (except in the central depression(s) 44).

Referring again to FIG. 9, the second absorbent cores 35 shaped in the second molding station 52 are successively laminated on the upper surface of the respective first absorbent cores 34 having been press-worked in the first press station 66. The above-mentioned absorptive material (M2) is fed through a feed conduit 58 toward an outer peripheral surface of a second rotary suction drum 57 and successively deposited in respective recessed molds 71 formed thereon. In this manner, the second absorbent cores 35 are molded (pre-formed) to have a substantially uniform thickness over the whole areas thereof. The pre-formed second absorbent cores 35 may, but not necessarily, have a substantially uniform mass per unit area throughout an entirety (whole area) thereof. The pre-formed second absorbent cores 35 are transferred by means of a delivery suction roller 72 underlying the second rotary suction drum 57 and rotating in a direction opposite to the direction in which the second rotary suction drum 57 rotates onto a second conveyor belt 59. The pre-formed second absorbent cores 35 transferred onto the second conveyor belt 59 in this manner run in a direction opposed to the machine direction MD and are successively compressed (press-worked) over the whole areas thereof, at the second press station 73, between a second press roller 74 having a smooth peripheral surface and a second anvil roller 75 opposed to the second press roller 74. The press-working does not significantly change the mass per unit area of the second absorbent cores 35. Therefore, if the pre-formed second absorbent cores 35 have a substantially uniform mass per unit area throughout an entirety thereof, the second absorbent core 35 in the final product still includes the substantially uniform mass per unit area over its entirety.

Then, at a laminating station 53, the second absorbent cores 35 are successively laminated on the upper surface of the respective first absorbent cores 34 loaded on the first conveyor belt 55 underlying the second conveyor belt 59 and moving in the machine direction MD. A driving roller 76 for the second conveyor belt 59 has a peripheral velocity regulated so as to assure that the second absorbent cores 35 be laminated on the intermediate sections of the respective first absorbent cores 34. By following these steps, the absorbent layer 15 of a two-layered structure includes the first and second absorbent cores 34, 35. Though not illustrated, the process may include a step of wrapping the absorbent layer 15 with a wrapping sheet of liquid-dispersant tissue paper or the like. While a plurality of the recessed molds 60, 71 formed on the first rotary suction drum 56 and the second rotary suction drum 57, respectively, are illustrated and described so as to be spaced one from another in the respective circumferential directions, it is possible to arrange these recessed molds 60, 71 not intermittently but contiguously, respectively. Furthermore, while the step of making the second absorbent core 35 has been exemplarily described above, it is also possible to place a delivery roller 72 above the first conveyor belt 55 (without installing the second conveyor belt 59) so that the second absorbent cores 35 may be directly laminated on the upper surfaces of the respective first absorbent cores 34.

Figure 11:
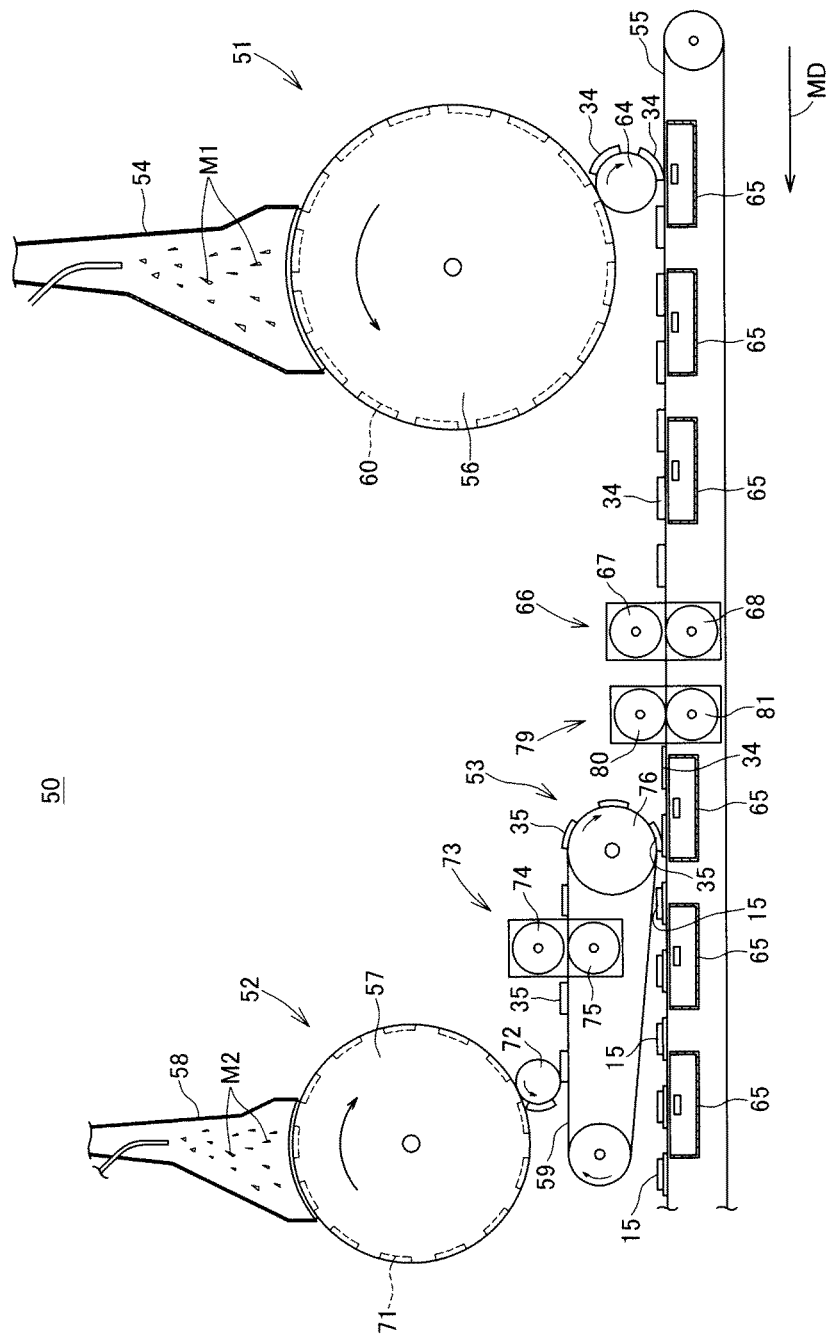
FIG. 11 is a perspective view illustrating the apparatus according to another embodiment.
Figure 12:
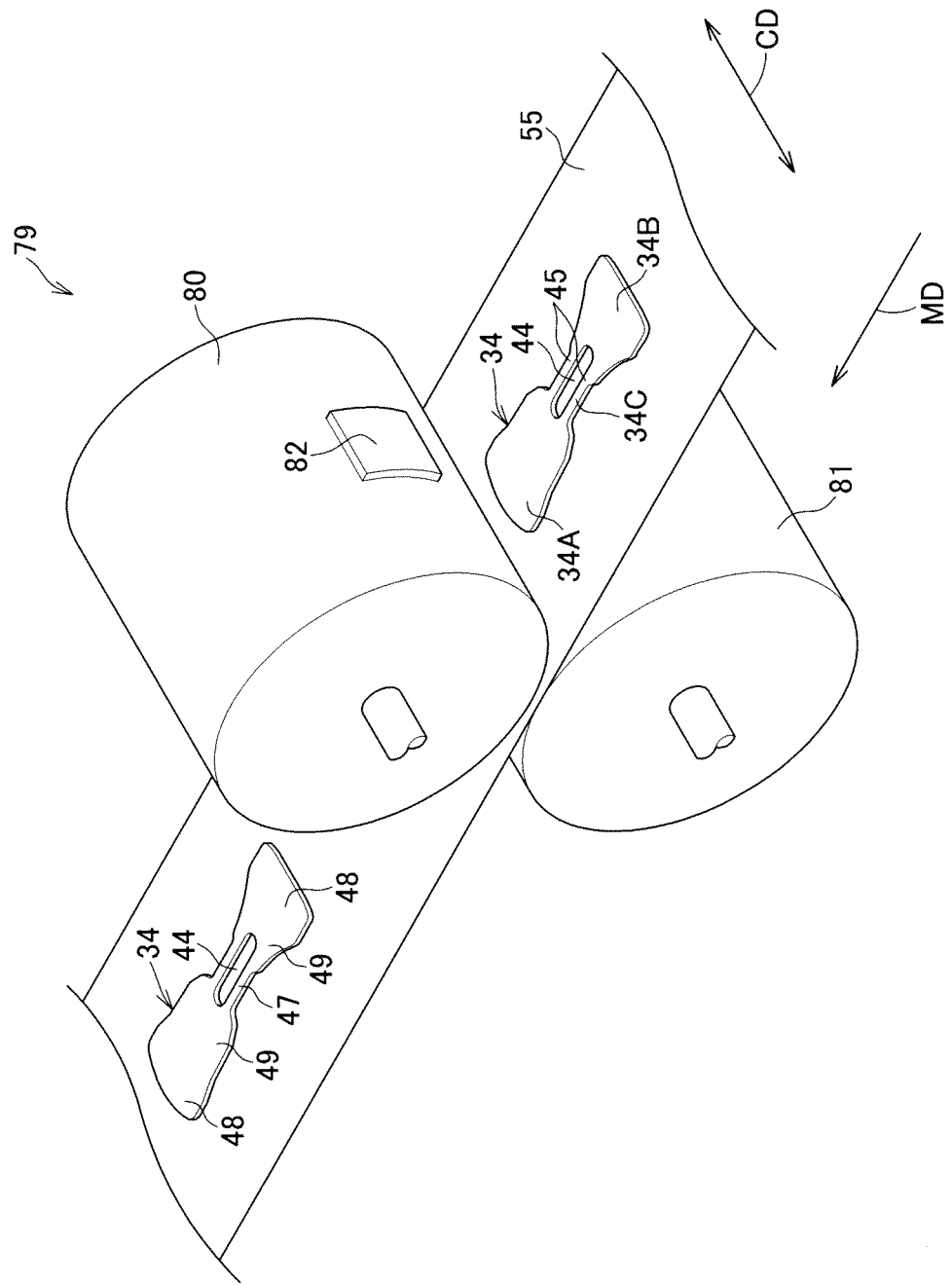
FIG. 12 is a perspective view illustrating a second press station in the apparatus.

Referring to FIG. 11, the apparatus 50 according to the present embodiment for making the absorbent layer 15 includes a third press station (press-working station) 79 defined on the downstream side of the first press station 66 so that the first absorbent cores 34 having been press-worked may be further press-worked at this third press station 79. As illustrated in FIG. 12, the third press station 79 includes a third press roller 80 and a third anvil roller 81 opposed thereto so as to cooperate with the third press roller 80 wherein the third press roller 80 is intermittently formed on substantially midsections in the cross direction CD of its outer peripheral surface with substantially rectangular protrusions 82. At the third press station 79, a peripheral velocity of the third press roller 80 is controlled in accordance with a conveying velocity of the first absorbent cores 34 so that the protrusions 82 on the third press roller 80 press-work exclusively the intermediate sections 34C of the first absorbent cores 34 which have been press-worked in the first press station 66. According to the present embodiment, the intermediate sections 34C of the first absorbent cores 34 are locally press-worked in the third press station 79 and, in consequence, the high density zones 47 of the respective first absorbent cores 34 which have been press-worked in the third press station 79 can be further enhanced in density as well as stiffness in comparison to the remaining zones. At the respective press stations (press-working steps), it is possible to press-work the first absorbent cores 34 and/or the second absorbent cores 35 in multiple courses of press-working by the respective additional pairs of press rollers. In such case, the pressure exerted by the respective press rollers to the absorbent cores may be gradually or stepwise decreased and/or the clearance defined between the respective press rollers and the associated anvil rollers may be gradually or stepwise decreased to assure that the conveying velocity can be improved without making the material get jammed.

Second Embodiment

Figure 13:
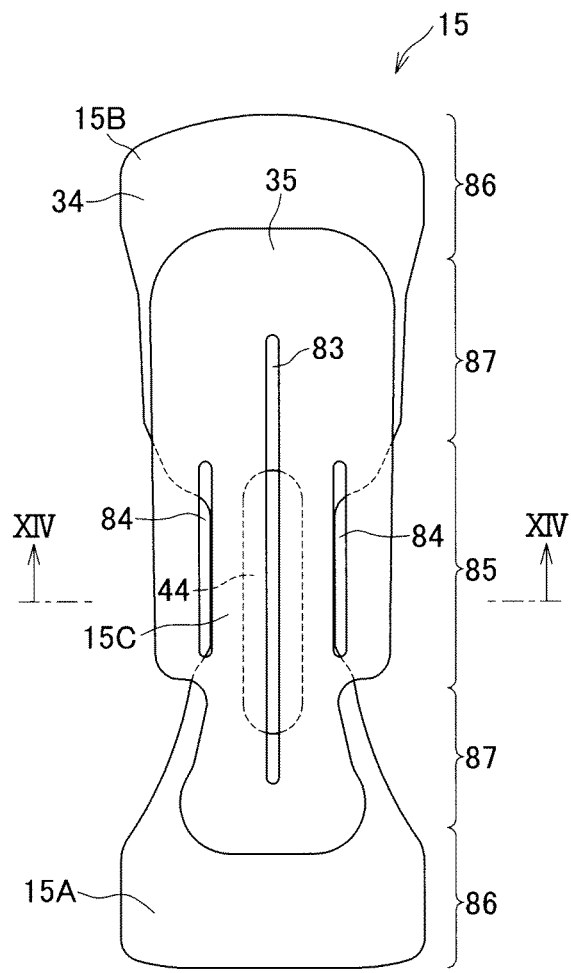
FIG. 13 is a plan view of the absorbent layer according to a second embodiment of the present invention.

Only the features distinguished from those of the first embodiment will be described hereunder with reference to FIG. 13. The absorbent layer 15 is of a two-layered structure including the first absorbent core 34 defining the lower layer and the second absorbent core 35 defining the upper layer, wherein the second absorbent core 35 is formed in its intermediate section with a slender (further) central depression 83 extending in the longitudinal direction Y and a pair of lateral depressions 84. The absorbent layer 15 according to the present embodiment may be obtained by a process which is alternative to the above-mentioned manufacturing process. Specifically, the second absorbent core 35 may be stacked upon the upper surface of the first absorbent core 34 and these absorbent cores may be press-worked together and thereby a high density zone 85, low density zones 86 and moderate density zones 87 are formed. A basis mass of the absorbent layer 15 is higher in the first region defined by the first absorbent core 34 and the second absorbent core 35 laminated together than in the second region defined by the first absorbent core 34 alone or by the second absorbent core 35 alone. Consequentially, after being press-worked by the press roller, the first region becomes higher than the second region in density as well as in stiffness. In the first region in which the first absorbent core 34 and the second absorbent core 35 are laminated together, the central section 15C including the central depression 83 and the lateral depressions 84 of the second absorbent core 35 and the central depression 44 of the first absorbent core 34 are higher in both density and stiffness than the remaining sections. This is because an area (pressurized contact area) over which the intermediate section 15C comes in contact with the first press roller 67 under a pressure is smaller than that of the remaining sections. In this way, the absorbent layer 15 can be formed with the high density zone 85, the moderate density zones 87 and the low density zones 86.

Figure 14:
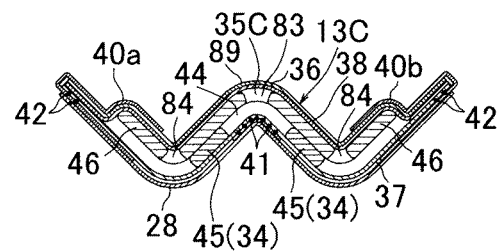
FIG. 14 is a sectional view taken along line XIV-XIV in FIG. 13.
Figure 15:
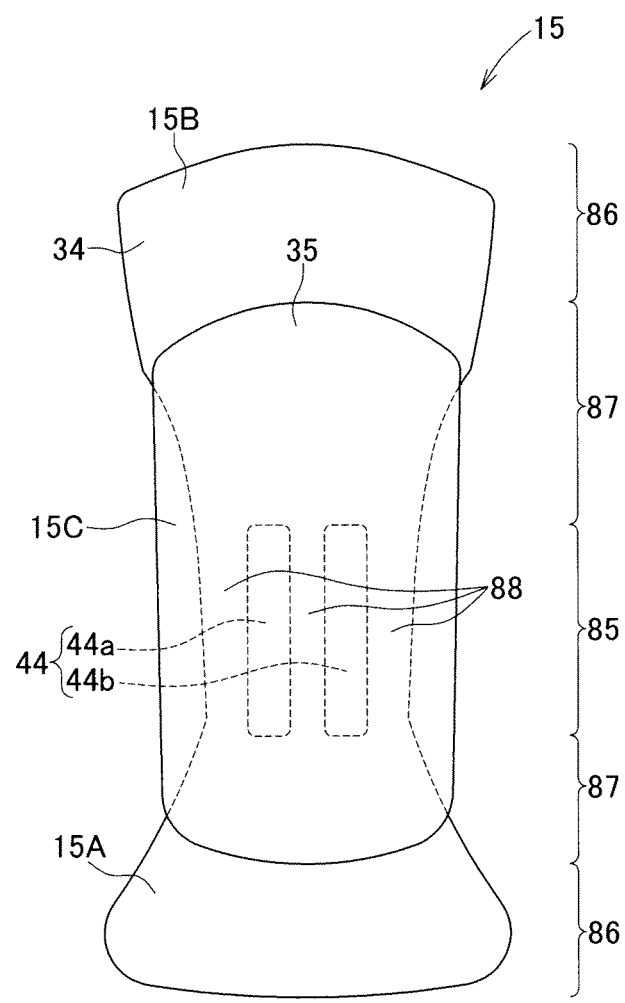
FIG. 15 is a plan view of the absorbent layer according to a third embodiment.

Referring to FIG. 14, the second absorbent core 35 may be formed with the second central depression 83 and the lateral depressions 84 to facilitate a central convex region 89 to be folded along the second central depression 83 functioning as the fold guiding means, and to facilitate the lateral extensions 46 of the second absorbent core 35 to be folded along the lateral depressions 84 defining a boundary between regions of different stiffness values. In this way, the midsection 13C of the crotch region 13 can be reliably and regularly folded substantially in a W-shape. Alternative arrangements are also possible as long as the above-mentioned effect can be assured. For example, at least one of the second central depression 83 and the lateral depressions 84 may be eliminated or the two-layered structure may be rearranged so that the first absorbent core 34 defines the upper layer and the second absorbent core 35 defines the lower layer.

Third Embodiment

Only the features distinguished from those of the first embodiment will be described hereunder in reference to FIG.

15. According to the present embodiment, the absorbent layer 15 is of a two-layered structure including the first absorbent core 34 defining the lower layer and the second absorbent core 35 defining the upper layer wherein the first absorbent core 34 is formed in its intermediate section with central depressions including a pair of depressions 44a, 44b extending in the longitudinal direction Y. In the intermediate section of the absorbent layer 15, the second absorbent core 35 and the first absorbent core 34 overlap each other along outer sides of the respective depressions 44a, 44b as viewed in the transverse direction X and also between these depressions 44a, 44b to define high stiffness zones 88. The absorbent layer 15 according to the present embodiment may be obtained by a process which is alternative to the above-mentioned manufacturing process. Specifically, the second absorbent core 35 may be stacked upon the upper surface of the first absorbent core 34 and this assembly may be press-worked together and thereby a high density zone 85, low density zones 86 and moderate density zones 87 are formed. With such construction, the intermediate section 13C of the crotch region 13 can be easily and regularly folded substantially in a W-shape as viewed in the cross-section along the side edges of the depressions 44a, 44b and/or the high stiffness zones 88.

Fourth Embodiment

Figure 16:
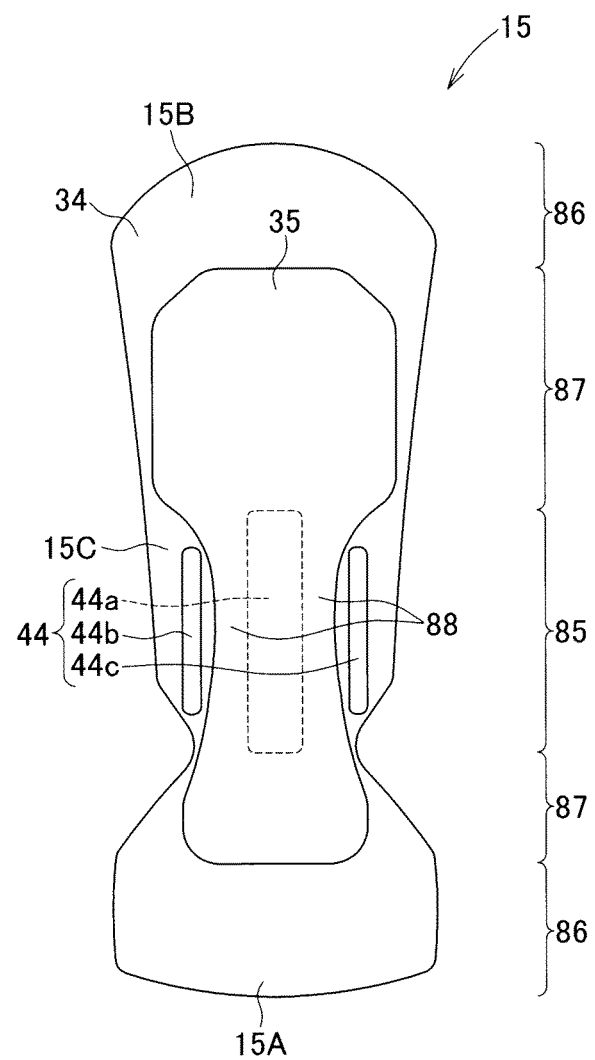
FIG. 16 is a plan view of the absorbent layer according to a fourth embodiment.

Only the features distinguished from those of the first embodiment will be described hereunder in reference to FIG. 16. According to the present embodiment, the absorbent layer 15 is of a two-layered structure including the first absorbent core 34 defining the lower layer and the second absorbent core 35 defining the upper layer wherein the intermediate section of the absorbent layer 15 is formed with the central depression 44 including a relatively wide (wider) depression 44a centrally extending in the longitudinal direction Y and a pair of width-constricted (narrower) depressions 44b, 44c which are narrower than the central depression 44a and extending on both sides of the central depression 44a. In the second absorbent core 35, the intermediate section is narrower than that of the first absorbent core 34, and the section lying on the side of the front end section 15A of the absorbent layer 15 is narrower than the section lying on the side of the rear end section 15B of the absorbent layer 15. In consequence, the narrow width grooves 44b, 44c extend outside the opposite side edges of the second absorbent core 35. In the absorbent layer 15, the second absorbent core 35 overlaps the first absorbent core 34 in the region defined between the narrow width depressions 44b, 44c and the wide depression 44a formed in the intermediate section to form the high stiffness zones 88. The absorbent layer 15 according to the present embodiment may be obtained by a process which is alternative to the above-mentioned manufacturing process. Specifically, the second absorbent core 35 may be stacked upon the upper surface of the first absorbent core 34 and this assembly may be press-worked together to form the high density zone 85, the low density zones 86 and the moderate density zones 87. With such construction, the intermediate section 13C of the crotch region 13 can be easily and regularly folded substantially in a W-shape as viewed in the cross-section along the side edges of the depressions 44a, 44b and/or the high stiffness zones 88. It is possible to arrange so that the narrow width depressions 44b, 44c partially overlap the opposite side edges of the second absorbent core 35 as long as the effect as has been described above is assured.

Fifth Embodiment

Only the features distinguished from those of the first embodiment will be described hereunder with reference to FIG. 17. The absorbent layer 15 is a single-core absorbent layer and has an outer shape similar to the common boundary defined by both the first and second absorbent layers 34, 35 overlapping each other in the previously described embodiments. The absorbent layer 15 is formed with a central depression 90 extending in the longitudinal direction Y. Although a width dimension of the absorbent layer 15 in the transverse direction X does not significantly varies from the intermediate section 15C toward the front and rear end section 15A, 15B, the intermediate section 15C is formed with the central depression 90 to define narrow width regions 91.

Figure 17:
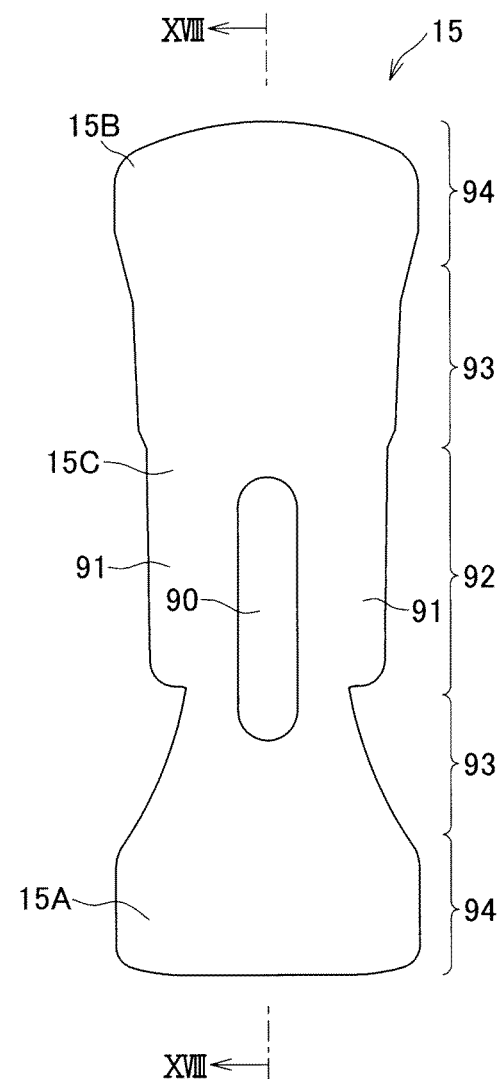
FIG. 17 is a plan view of the absorbent layer according to a fifth embodiment.
Figure 18:
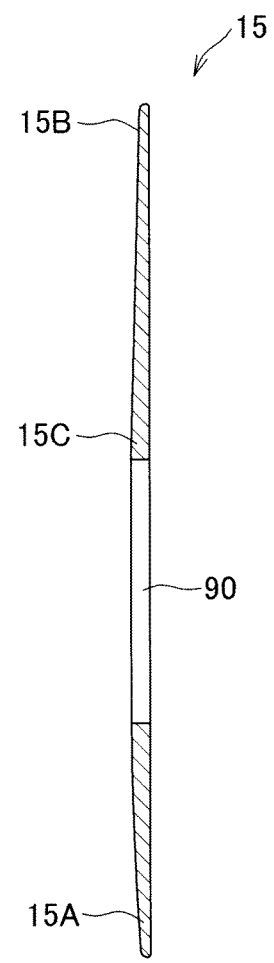
FIG. 18 is a sectional view taken along line XVIII-XVIII in FIG. 17.

Referring to FIGS. 17 and 18, the basis mass as well as the thickness dimension, i.e., the bulkiness of the absorbent layer 15 is higher in the narrow width regions 91 than the remaining regions. In other words, the basis mass is gradually (or stepwise) reduced and the thickness dimension is also gradually (or stepwise) reduced from the intermediate section 15C toward the front and rear end sections 15A, 15B and the absorbent layer 15 is formed with the high density zone 92, the moderate density zones 93 and the low density zones 94.

The component members of the diaper 10 are not limited to those described in this specification but the other various types of materials widely used or to be developed in the relevant technical field may be used without limitation. The terms "first", "second" and "third" used in the specification and claims of the present application are used merely to distinguish similar or related elements, similar or related positions or other similar or related means. The application of various embodiments disclosed herein is not limited to disposable diapers, but also to other products where liquid absorbency is desirable, such as, disposable toilet-training pants, disposable incontinent diapers, disposable menstruation pants etc, and methods of manufacturing the same.

A first aspect described above may be summarized as follows:

An absorbent layer for a disposable wearing article having a longitudinal direction and a transverse direction orthogonal to the longitudinal direction, and including a front region and a rear region, wherein:

the absorbent layer includes an absorbent core formed from at least one of fluff wood pulp and superabsorbent polymer particles, and has transversely extending front and rear end sections and an intermediate section lying between the front and rear end sections;

at least the intermediate section of the absorbent layer is formed with a central depression extending in the longitudinal direction;

the absorbent core has a mass per unit area substantially uniform over an entire area thereof, except in a region corresponding to the central depression; and the absorbent layer has, on both sides of the central depression, high density zones each having a density higher than those in the front and rear end sections.

The first aspect may include at least the following embodiments.

(1) The intermediate section is narrower than the front and rear end sections.

(2) The absorbent layer has a shape gradually becoming narrower from the front and rear end sections toward the intermediate section and a density gradually decreasing from the front and rear end sections toward the intermediate section to define the high density zones lying in the intermediate section, low density zones lying in the front and rear end sections, and moderate density zones lying between the high density zones and the low density zones.

(3) The central depression includes a pair of depressions extending in the longitudinal direction.

(4) The absorbent layer includes a first absorbent core and a second absorbent core layered on an upper or lower surface of the first absorbent core, wherein the first absorbent core has a front end section lying on the front region, a rear end section lying on the rear region and an intermediate section lying between these front and rear end regions; and the intermediate section of the first absorbent core is formed with the central depression extending in the longitudinal direction and is formed, on both sides of the central depression, with the high density zones having a density higher than those in the front and rear end sections of the first absorbent core.

(5) The first absorbent core and the second absorbent core have a substantially uniform mass per unit area over the whole area thereof.

(6) The second absorbent core has a dimension in the longitudinal direction smaller than that of the first absorbent core, and an intermediate section of the second absorbent core overlapping the intermediate section of the first absorbent core is wider than the intermediate section of the first absorbent core.

(7) The intermediate section of the second absorbent core is formed with a further central depression extending in the longitudinal direction.

(8) The intermediate section of the second absorbent core is formed with lateral depressions on both sides of the further central depression as viewed in the transverse direction and extending in the longitudinal direction.

(9) The central depression of the first absorbent core comprises a pair of depressions extending in the longitudinal direction.

(10) The second absorbent core has a dimension in the longitudinal direction smaller than that of the first absorbent core, the intermediate section of the second absorbent core overlapping the intermediate section of the first absorbent core is narrower than the intermediate section of the first absorbent core, and the central depression of the first absorbent core comprises a wider depression extending in the longitudinal direction and narrower depressions extending on both sides of the wider depression as viewed in the transverse direction.

(11) The absorbent layer includes a crotch region between the front and rear regions, and a crotch elastic element extending in the longitudinal direction so as to at least partially overlap the central depression.

(12) The absorbent layer has the high density zones lying in the intermediate section, low density zones lying in the front and rear end sections, and moderate density zones lying between the high density zones and the low density zones.

A second aspect described above may be summarized as follows.

A method for making an absorbent layer for a disposable wearing article including the steps of:

successively depositing absorptive materials including at least one of fluff wood pulp and superabsorbent polymer particles into recessed molds, which are formed on an outer peripheral surface of a rotary suction drum and centrally provided with protrusions, to mold absorbent cores having a substantially uniform thickness over the whole areas thereof, except in central depressions corresponding to the protrusions, and respectively having intermediate sections narrower than front and rear end sections thereof;

successively conveying the pre-formed absorbent cores in a machine direction; and at a press-working station including a press roller set arranged to exert a predetermined force to a rotary shaft of an anvil roller provided in opposition to the press roller, successively guiding the pre-formed absorbent cores into a clearance defined between the press roller and the anvil roller for press-working the respective absorbent cores and forming the intermediate sections of the respective absorbent cores with high density zones on both sides of the respective central depressions.

The second aspect may include at least the following embodiments.

(1) The method further includes the steps of:

successively depositing absorptive materials including at least one of fluff wood pulp and superabsorbent polymer particles into recessed molds, which are formed on an outer peripheral surface of a second rotary suction drum, to mold second absorbent cores having a substantially uniform thickness over the whole areas thereof;

successively conveying the pre-formed second absorbent cores;

at a second press-working station including a second press roller and a second anvil roller provided in opposition to the second press roller, successively press-working the individual pre-formed second absorbent cores over the whole areas thereof; and laminating the press-worked second absorbent cores onto the associated press-worked first absorbent cores to form absorbent layers.

(2) The method further includes the steps of:

additionally setting up, on the downstream side of the first press-working station, a third press-working station including a third press roller intermittently provided in a midsection of a peripheral surface thereof with protrusions and a third anvil roller opposed to the third press roller; and controlling a peripheral velocity of the third press roller in accordance with a conveying velocity of the conveying means to assure that the protrusions on the peripheral surface of the third press roller press-work exclusively the intermediate sections of the press-worked absorbent cores.

The described aspects and/or embodiments provide one or more of the following effects.

The absorbent layer is improved so that one or more high density zones can be locally formed on the absorbent layer by a relatively simplified method and, when a disposable article is worn, a midsection of a crotch region can be regularly deformed without losing shape.

Further, the high density zones are formed on both sides of the central depression lying in the intermediate section of the absorbent layer. With this arrangement, the midsection of the crotch region can be stably shaped so that the midsection may be convexly folded toward the wearer's body.

Still further, the absorbent core(s) forming the absorbent layer has a substantially uniform basis mass over its entire area and it is not necessary to locally increase the basis mass of the absorbent core or to attach separately prepared member in order to form the high density zone. Consequentially, the process for making the article is relatively simple and no additional cost is required.

This application claims the benefit of Japanese Application No. 2010-286757 and Japanese Application No. 2011-259431 the entire disclosures of both of which are incorporated by reference herein.

The invention claimed is:

1. An absorbent layer for a disposable wearing article having a longitudinal direction and a transverse direction orthogonal to the longitudinal direction, and comprising:

a front region and a rear region, a first absorbent core formed from at least one of fluff wood pulp and superabsorbent polymer particles, and having transversely extending front and rear end sections and an intermediate section lying between the front and rear end sections, a second absorbent core layered on an upper or lower surface of the first absorbent core, wherein at least the intermediate section of the first absorbent core is formed with a central depression extending in the longitudinal direction, the first absorbent core has a mass per unit area substantially uniform over an entire area thereof, except in a region enclosed by the central depression, the first absorbent core has, on sides of the central depression, high density zones outside the central depression, each high density zone having a density higher than the front and rear end sections, the second absorbent core has a dimension in the longitudinal direction smaller than that of the first absorbent core, an intermediate section of the second absorbent core overlapping the intermediate section of the first absorbent core is narrower than the intermediate section of the first absorbent core, and the central depression of the first absorbent core comprises a wider depression extending in the longitudinal direction and narrower depressions extending on sides of the wider depression as viewed in the transverse direction.

2. The absorbent layer defined by claim 1, wherein the intermediate section of the first absorbent core is narrower than the front and rear end sections.

3. The absorbent layer defined by claim 1, wherein the absorbent layer has a shape gradually becoming narrower from the front and rear end sections toward the first core intermediate section, and a density increasing from the front and rear end sections toward the first core intermediate section to define the high density zones lying in the first core intermediate section, low density zones lying in the front and rear end sections, and moderate density zones lying between the high density zones and the low density zones.

4. The absorbent layer defined by claim 1, wherein the central depression comprises a pair of narrower depressions extending in the longitudinal direction.

5. The absorbent layer defined by claim 1, wherein the second absorbent core has a substantially uniform mass per unit area over a whole area thereof.

6. The absorbent layer defined by claim 1, further comprising: a crotch region between the front and rear regions, and a crotch elastic element extending in the longitudinal direction so as to at least partially overlap the central depression.

7. The absorbent layer defined by claim 1, wherein the absorbent layer has the high density zones lying in the first absorbent core intermediate section, low density zones lying in the front and rear end sections, and moderate density zones lying between the high density zones and low density zones.

* * * * *